(12) United States Patent
Lee et al.

(10) Patent No.: US 7,692,160 B2
(45) Date of Patent: Apr. 6, 2010

(54) METHOD AND SYSTEM OF OPTICAL IMAGING FOR TARGET DETECTION IN A SCATTERING MEDIUM

(75) Inventors: Deborah Stutz Lee, Niskayuna, NY (US); Kajoli Banerjee Krishnan, Bangalore (IN); Siavash Yazdanfar, Schenectady, NY (US); Stephen Johnson Lomnes, Philadelphia, PA (US); Floribertus P. M. Heukensfeldt Jansen, Ballston Lake, NY (US); Stephen Andrew Latham, Kalamazoo, MI (US)

(73) Assignee: General Electric Company, Niskayuna, NY (US)

( * ) Notice: Subject to any disclaimer, the term of this patent is extended or adjusted under 35 U.S.C. 154(b) by 342 days.

(21) Appl. No.: 11/756,135

(22) Filed: May 31, 2007

(65) Prior Publication Data
US 2008/0296482 A1    Dec. 4, 2008

(51) Int. Cl.
*G01J 1/58* (2006.01)
(52) U.S. Cl. .................. 250/458.1; 250/459.1
(58) Field of Classification Search .............. 250/458.1, 250/459.1; 356/417
See application file for complete search history.

(56) References Cited

U.S. PATENT DOCUMENTS

| | | | |
|---|---|---|---|
| 5,355,215 A | 10/1994 | Schroeder et al. |
| 5,865,754 A | 2/1999 | Sevick-Muraca et al. |
| 5,943,129 A | 8/1999 | Hoyt et al. |
| 5,986,271 A | 11/1999 | Lazarev et al. |
| 6,239,868 B1 | 5/2001 | Jung et al. |
| 6,615,063 B1 | 9/2003 | Ntziachristos et al. |
| 6,958,815 B2 | 10/2005 | Bevilacqua et al. |
| 6,992,762 B2 | 1/2006 | Long et al. |
| 2003/0076571 A1 | 4/2003 | MacAulay et al. |
| 2004/0243198 A1 | 12/2004 | Heacock et al. |

OTHER PUBLICATIONS

M. A. A. Neil, R. Juškaitis, and T. Wilson; "Method of obtaining optical sectioning by using structured light in a conventional microscope"; Dec. 15, 1997 / vol. 22, No. 24 / Optics Letters; pp. 1905-1907.
Joshi Amit et al., "Non-contact Fluorescence Optical Tomography With Scanning Patterned Illumination", Optics Express, Jul. 10, 2006, vol. 14, No. 14, pp. 6516-6534.
PCT Search Report—Aug. 26, 2008.

*Primary Examiner*—David P Porta
*Assistant Examiner*—Mark R Gaworecki
(74) *Attorney, Agent, or Firm*—Jennifer E. Haeckl (57) ABSTRACT

A method and system for fluorescence imaging of a target in a subject comprising a scattering medium is provided. The method comprises illuminating one or more points on a surface of the scattering medium using an illumination source, wherein the plurality of points define an illumination region, collecting emitted light from an illumination region and an area away from the illumination region, and generating an image of the scattering medium using the emitted light.

21 Claims, 5 Drawing Sheets

METHOD AND SYSTEM OF OPTICAL IMAGING FOR TARGET DETECTION IN A SCATTERING MEDIUM

BACKGROUND

The invention relates to optical imaging systems and methods, and more particularly to fluorescence imaging of light scattering media.

In vivo imaging of biological tissues facilitates early detection of disease, thereby providing an opportunity for reliable and pro-active diagnosis of diseased tissues. Fluorescence imaging is an example of a powerful non-invasive imaging technique that has been used in various applications in biological sciences. For example, fluorescence imaging is applied in fields such as genetic sequencing, biomedical diagnostics, and flow cytometry. Typically, fluorescence imaging systems include a light source which illuminates the subject to be imaged. The tissue inside the subject fluoresces either endogenously or exogenously in response to the excitation illumination, and this resulting emission is imaged to obtain information about the interior composition of the subject.

Fluorescence imaging is generally hampered by poor signal-to-noise ratio of fluorescent targets located within a subject. Much of this noise is caused by reflection of the excitation light from the surface, and by strong fluorescence signals emitted from points near the surface of the subject. Fluorescence imaging may be of different types, such as continuous wave, frequency domain, or time domain, and with each method the illumination and detection schemes are typically (a) point source illumination and point detection, or (b) planar illumination and full-field detection.

The point source illumination and point detection technique employs single pixel scanning for greater sensitivity, but this method may be very slow in generating a high-resolution image of the subject. In planar illumination with full-field detection, the entire area of the subject is illuminated and imaged, and while this method is capable of rapidly generating high-resolution images, it has poor sensitivity due to the low signal to noise ratio. The reflection of the excitation source increases the noise, and the limited amount of power that can be applied to the subject in full-field illumination mode limits the possible detected fluorescence signal in an absorbing medium such as tissue. Both the increased noise and limited signal contribute to a lower signal-to-noise ratio. Continuous wave planar illumination full-field imaging is also limited in its ability to determine the depth of the target.

Accordingly, there is a need for imaging systems and methods that can provide a high resolution, high sensitivity image in a shorter period of time.

BRIEF DESCRIPTION

In an exemplary embodiment, a method for fluorescence imaging of a target in a subject comprising a scattering medium is provided. The method comprises illuminating a plurality of points on a surface of the scattering medium using a source, wherein the plurality of points define an illumination region, collecting emitted light from an illumination region and an area away from the illumination region, and generating an image of the scattering medium using the emitted light.

In another exemplary embodiment, a system for imaging a target in a subject is provided. The system comprises a source configured to illuminate at least a portion of a surface of the subject by a patterned illumination, a full-field imaging detector configured to acquire emitted light from the surface of a subject, and a processor to transform the acquired emitted light into a display image.

In another exemplary embodiment, a method for imaging targets in a subject is provided. The method comprises illuminating a plurality of locations on a surface of the subject with a patterned illumination, collecting corresponding emitted light in a plurality of image frames from areas within and away from illumination regions, and generating an image of the scattering medium using the emitted light.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Described herein are fluorescence imaging methods and systems. In embodiments of the invention, a surface of a subject having a scattering medium is illuminated at one or more points and the corresponding emitted light is collected from an illumination region, as well as from the regions away from the illumination region. As used herein, the term "point" refers to a small area of illumination of the order of 1 mm square. In some embodiments, the subject is illuminated using a patterned illumination combined with area detection. As used herein, the term "patterned illumination" refers to light incident on a subject that is to be imaged such that the light is in the form of one or more points that collectively form a determined pattern on a surface of the subject. As used herein, the term "area detection" may refer to detection of emitted light from the illumination region, but more typically refers to detection of emitted light from regions that are away from the illumination regions". In certain embodiments, the detection area may be around 1 mm to about 25 mm away from the illumination region. In some embodiments, the distance of the detection area may vary depending on the size of the subject. For example, the distance between the illumination region and the detection area may increase with an increase in size of the subject. When a light source shines patterned illumination onto the surface of the subject. The target inside the subject fluoresces in response to the patterned illumination or the excitation source, thereby producing emitted light. It should be noted that the terms "patterned illumination" and "excitation light" may be used interchangeably throughout the application For fluorescence imaging, filters may be employed to block the excitation light that may be reflected by the surface of the subject from reaching the area detector, so that only the emitted light is detected. Such filters could be wavelength specific bandpass, bandstop, highpass, lowpass, polarizer, neutral density, or spatially varying. As the distance from illumination region to detection point increases, the amount of reflected light and near-surface fluorescence decreases, reducing the noise and increasing the signal-to-noise ratio to improve the detection of emitted light, thereby, increasing the sensitivity of the imaging system. The area detector samples the emitted fluorescence at many different source to detector separations. As used herein, the term "source to detector separation" refers to a distance from a point in the illumination region on the surface of the subject to a point in the area of where the emitted light is detected on the surface of the subject. Further, for the purpose of measuring the distances, the location of the predetermined illumination may be considered to be the geometric center point of the pattern of the patterned illumination, the centroid of illumination intensity, or the closest distance between the source and the detector, depending on the size, shape, and the spatial uniformity of the illumination intensity. If the illumination is uniform over the region, the source to detector distance would be the closest distance between the illumination region and the detector location. Considering a small illumination region on the surface of the subject, the illumination region may have a distribution of intensities; therfore, the distance representation is more likely to be the distance between the centroid of the illumination region and the detector. Each pixel of a full-field detector, is considered a separate detector, so the center of the detection area is considered to be the location on the surface of the subject where emitted light is detected by a pixel. Different distances between the illumination region and the area of measured emitted light provide information about the depth of the target.

The use of patterned illumination allows for deeper penetration of the excitation light as compared to the planar illumination mainly because while employing the patterned illumination the light can be concentrated in a smaller area instead of being spread over the entire imaging surface of the subject, and thus higher local intensity may be used without exceeding average power limits. Additionally, full-field imaging techniques allow for faster imaging time as compared to point-by-point-techniques, where at any given time, only a single point on the surface of the subject, represented by a pixel in the resulting image, is illuminated by the excitation source and the resulting emitted light is detected at another point, or the same point. An image is created by repeating this measurement for all points in the image. Further, a combination of patterned illumination with an area detector generates images with a higher signal-to-noise ratio than full-field planar illumination system. Also, the combination of patterned illumination with an area detector requires less imaging time as compared to a point-by-point imaging system.

The continuous wave system is unable to discriminate two targets at the same horizontal location but at different depths. However, in embodiments of the present technique, different image frames corresponding to the different illumination source positions or different source to detector separations may be used to discriminate between single and stacked targets inside a source as will be described in detail with regard to FIG. 3. In certain embodiments of the present invention, one view of the imaging subject may be sufficient to image the stacked targets. As will be appreciated, stacked targets may be resolved with multiple views using imaging techniques such as continuous wave, frequency domain, or time domain. However, due to the location of the targets and the size of the imaging subject, multiple views may not always allow stacked targets to be resolved.

Reconstruction methods are used to interpret the two-dimensional (2D) image data into a three-dimensional (3D) representation of the target within the volume. Three-dimensional information may also represent fluorescence or absorption. As will be described in detail with regard to FIG. 1, the patterned illumination may be scanned over the subject, or the subject or imaging device may be moved to collect multiple views of the subject. The device could be used in industrial, small animal, and clinical situations including deep tissue imaging, surgery, and endoscopy. The imaging subject may be illuminated in a reflection mode or transmission mode. While imaging of biological tissue can rely on the natural optical properties of the endogenous molecules for providing optical contrast, in some embodiments, exogenous molecules may be introduced in the tissue to provide additional contrast. In this respect, exogenous chromophores as well as fluorophores may be used. Furthermore, the bio-distribution of such contrast agents may be followed. Following the distribution of the contrast agents in the subject, the optics as well as the source may be arranged to illuminate and detect light at one or more wavelengths. For example, the source and associated optics may be arranged to illuminate the surface of the subject with the determined patterned illumination and preferably at an excitation wavelength of a fluorophore, while the detector and associated optics may be arranged to detect light at an emission wavelength of the fluorophore. For example, the system may employ absorbing contrast agents, fluorescence agents, fluorescent gene reporter systems, quantum dots, or phosphor agents. The system may be used with a variety of types of light sources and means for generating patterned excitation. The system may be used in combination with other imaging techniques including X-ray, magnetic resonance imaging (MRI), computed tomography (CT), positron emission tomography (PET), single photon emission computed tomography (SPECT), or the like.

Figure 1:
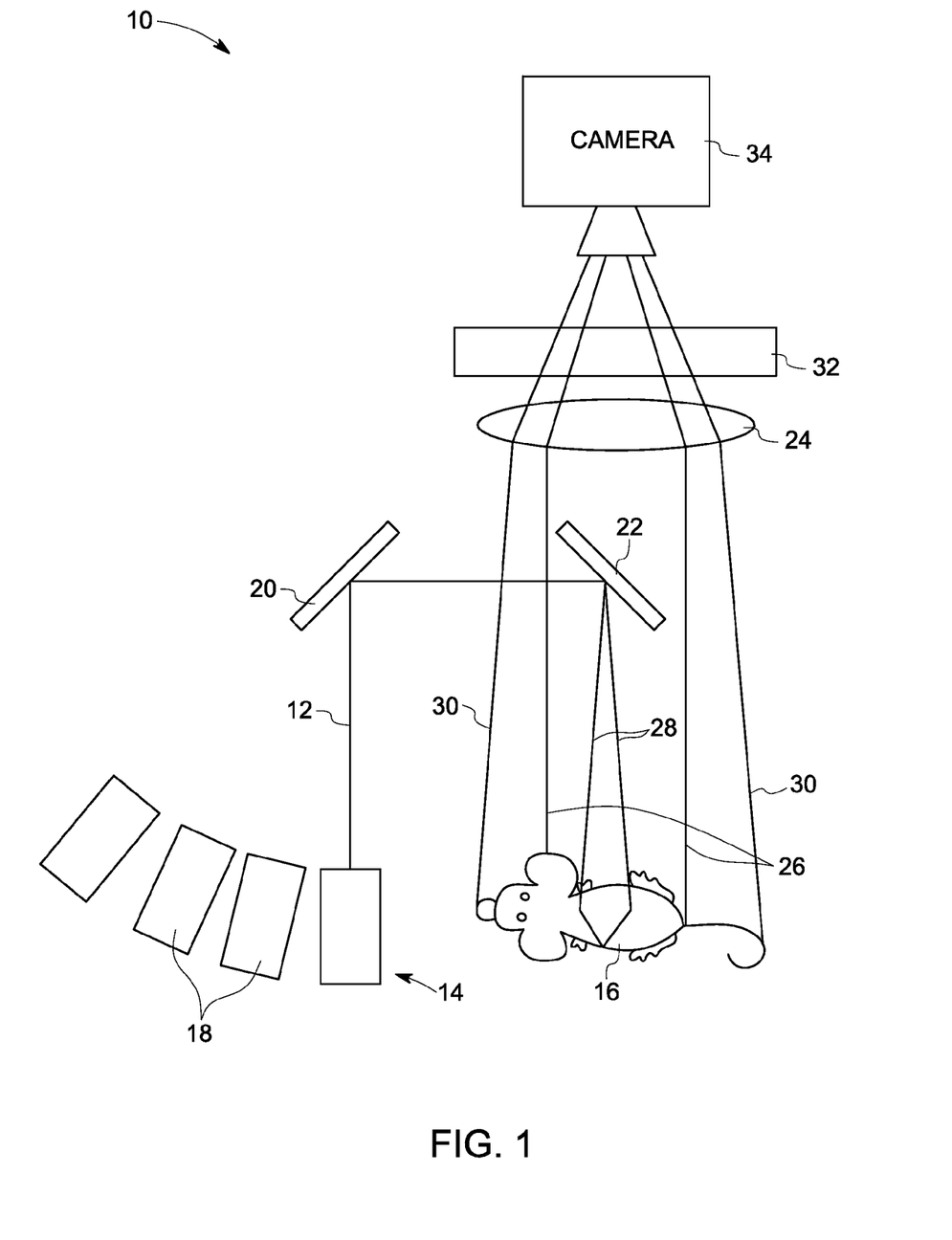
FIG. 1 is a schematic illustration of a fluorescence imaging system, in accordance with embodiments of the present technique.

With reference to FIG. 1 an embodiment of fluorescence imaging system 10 of the present invention is illustrated. Light 12 from an illumination source 14 is directed towards a subject 16. The system 10 of the illustrated embodiment is employed to image biological tissues or the target (not shown) inside the subject 16. It should be noted that although the illustrated embodiment is related to small animals such as a mouse, the imaging system 10 and the associated method of imaging may also be employed to larger animals and humans.

In the illustrated embodiment, the system 10 includes an illumination source 14 to generate patterned illumination (not shown). As will be described in detail below, the system 10 is configured to determine the depth of the target located inside the subject 16. The depth of the target may be determined by varying the distances from the target position in proportion to the target depth and appropriately processing the detected image to determine target depth, for example. As used herein, the term "target position" refers to the position of the projected image of the target on the surface of the subject 16. In the illustrated embodiment, the illumination source 14 includes a plurality of laser diodes 18. The plurality of laser diodes 18 is employed to produce the light 12 in the form of a patterned illumination (not shown). In one example, the patterned illumination so produced may include multiple wavelengths. In these embodiments, the source 14 may include laser diodes, such that each laser diode is configured to emit at its own unique wavelength different from the wavelength emitted by the other laser diodes. Alternatively, a unique multi-wavelengths source of light may also be used. In the later case, ranges of wavelengths or a specific wavelength may be selected by using filters, gratings or the like. This selected wavelength(s) may then be allowed to excite the target. Although not illustrated, in place of laser diodes, the source 14 may include one or more of a continuous wave light source, a pulsed light source (e.g., a pulsed laser), a frequency modulated light source, an intensity modulated light source, a phase modulated frequency varying light source, or combinations thereof. The time and frequency domain methods enable extraction of information on parameters such as fluorescence lifetime, quantum yield, concentration, photon path length, etc.

Further, the patterned illumination may be scanned over a portion of a surface of the subject 16. Alternatively, the patterned illumination may be scanned over the entire surface of the subject 16. In some embodiments, the subject 16 may be scanned while keeping the patterned illumination spatially constant. In another embodiment, instead of the transverse motion, the subject 16 may be rotated along an axis. In these embodiments, the optics may be configured to adapt to the different tomographic configurations of the subject 16. Acquiring the image data while rotating the subject 16 provides variations in the distance between the surface and the target tissue because of the position of the tissue inside the subject 16 and also because of the change in contours of the subject 16. Accordingly, image construction may be improved by the use of an auto-focus system and by obtaining a profile of the scanned regions. Imaging the subject 16 while rotating it along an axis or by moving at least one of the subject and the patterned illumination with respect to each other, gives volumetric profile of the subject 16. In these embodiments, a simultaneous acquisition of image while rotating or moving the subject 16 gives a volumetric profile of the subject 16. This volumetric profile information assists in providing spatial information for image reconstruction and display. Further, the patterned illumination may be dynamically varied while imaging the subject 16. In these embodiments, either of the subject 16 or the patterned illumination may be made to move relative to the other.

A portion of the light 12 incident upon the surface of the subject 16 may penetrate the skin of the subject 16 and the remaining part may be reflected at the air/skin boundary of the subject 16. The photons that are propagated within the subject 16 are absorbed and scattered, thereby producing a large number of photon paths. In biological tissues absorption may arise as a result of the presence of natural (endogenous) or exogenous chromophores while scattering is triggered by the presence of macromolecular structures such as proteins, lipids and the like which create inhomogeneities in the refractive index. The fraction of the light that is not absorbed ultimately exits the subject 16 by diffusing through the skin barrier at various distances from the illumination point. It can be appreciated that photons that have traveled deeper in the tissue will take a longer time to exit at the surface of the small animal. In optically homogeneous media the distance between the illumination point and the point at which given photons exit is related to the effective depth of the average path of the photons. Thus the greater the distance between the illumination and exit points the greater the depth. While biological tissues are not optically homogeneous, still the distance between illumination points and the point of photon exit can also be considered to be related to the depth of the average path of photons. Deep penetrating photons emit from areas away from the illuminated region. This provides the basis for the area detection of the subject 16, while illuminating only a portion of an exposed surface/area of the subject 16. The optical signal collected from the subject 16 in such a way provides useful information about the optical properties of a region of interest. This information may be extracted and incorporated into image reconstruction algorithms.

As will be appreciated, the wavelength of the source 14 may be chosen based upon the fluorophore used for the target tissue. Frequency domain imaging may also be used with the patterned illumination to generate phase data from which the lifetime of the fluorescence may be determined. Fluorescence lifetime allows one to differentiate fluorescent agents, permitting the rejection of auto-fluorescence, and to detect environmental changes, such as pH, around a given agent. This data may then be registered with other imaging modalities, such as computed tomography (CT), to simultaneously provide structural and functional information.

As illustrated, the patterned illumination 28 is directed at the target 16 through associated illumination optics. The optics facilitates the movement of the patterned illumination 28 along the target 16. For example, the illumination optics may include a moveable reflective mirror 20, such as a mirror galvanometer. The beam of light 12 is reflected by the mirror galvanometer at a predetermined angle and directed towards a mirror 22. In some embodiments, the mirror 22 is a dichroic or a switching mirror. Typically, a dichroic or switching mirror is used for either sequential or simultaneous illumination of the subject 16 at different wavelengths. Further, the mirror 22 may be configured to reflect the light beam 12 in the form of a patterned illumination 28 in a direction substantially perpendicular to the surface of the subject 16 being scanned. It should be noted that a partial rotation of the reflective mirror 20 will modify the predetermined angle in which the light beam 12 is reflected by the reflective mirror 20, thereby directing the beam 12 to a different point on the mirror 22 and, consequently, to a different illumination region on the surface of the subject 16. In some embodiments, successive partial rotations of the reflective mirror 20 may be used to produces a line scan.

In addition to the illustrated optics, other lenses and filters may be employed in the illumination optics to focus the beam at the desired location on the subject 16, and to regulate the intensity of the excitation light, that is the light incident on the subject 16. For example, a lens may be optionally positioned between the reflection mirror 20 and the mirror 22 such that the reflection mirror 20 is at a focal distance of the lens to provide telecentric imaging. Further, filters may also be positioned between the source 14 and the reflection mirror 20 to adjust the intensity of the light beam 12 incident on the subject 16 so as to avoid any damage to the target disposed inside the subject 16. Other optical components may be employed to generate a plurality of points of illumination from a single source; examples of such components include diffraction gratings and cylindrical lenses, many other methods of generating distinct patterns of illumination are well known in the art.

The system 10 further includes an arrangement for detecting the emitted light 26. The emitted light 26 is in response to the excitation light or patterned illumination represented by the reference numeral 28. Light 26 emitted from the subject 16 is collected by the collection optics 24, which may include one or more lenses, mirrors and filters. Typically, the collection optics 24 is located above the illumination optics, but may be offset so that the collection path is not blocked by the mirror 22 or other optical components. The angular position of the mirror 20 relative to the incoming light 12 and the detector determines which light source is illuminating the subject 16 is being sampled since only part of the light (corresponding to a given collection point) impinging on the mirror is reflected at the proper angle to reach the detector. Selective detection of the light from a given collection point may be further enhanced by optically coupling the mirror galvanometer 20 with lenses and/or filters. The emitted light indicated by the reference numeral 30 represents the total emitted light produced by the subject 16 as a result of the patterned illumination 28 scanning the surface of the subject 16. It should be noted that the emitted light 30 that is shown to be emerging from the entire upper surface of the subject 16 may or may not be in response to the patterned illumination scanning the entire upper surface of the subject 16 at a given time. For example, in one embodiment, only a portion of the upper surface of the subject 16 may be illuminated with the patterned illumination, but the emitted light 26 may be collected from illuminated regions as well as from an area of interest away from the illuminated region. As mentioned above, in fluorescence imaging most of the noise is contributed by reflections of the excitation illumination, and also from fluorescence near the surface of the subject. Patterned illumination of the surface of the subject 16 accompanied by detection of the emitted light from areas away from the illumination region results in collection of relatively smaller amount of noise than in instances where the emitted light is collected from only the illuminated surface. As further described in FIG. 2, collecting the emitted light 26 from areas away from the illumination region decreases contribution from near surface fluorescence around the areas of interest, thereby resulting in improved sensitivity of detection at depth of the target, even in presence of a background signal.

The system 10 further includes a filter 32 configured to block excitation light that is reflected from the surface or from the near surface tissues of the target 16 from reaching the collection optics 24. In other words, the filter 32 is employed to further reduce the noise in the acquired image signals. The filter 32 may include one or more of a wavelength specific filter, a polarizing filter, a neutral density filter, or a spatially varying filter. The filter 32 may be such that it covers the entire area of the subject 16 from where the emitted light 26 is collected. Alternatively, the filter 32 may be configured to move along with the subject 16 or the patterned illumination such that the filter 32 is always in operation between the subject 16 and the detector 34. It is also possible to configure the system such that filter 32 selectively admits the excitation wavelength only; in that case the system can be used to obtain additional information about the optical properties of the subject which can be helpful in subsequent calculations of target depth and intensity. The detector 34 is configured to detect an area around the and away from the illuminated region. The detector 34 may be a full-field or multi pixel imaging device to capture an image of the emitted light or emitted fluorescence or scattered light emitted by the subject 16. A series of such images may be acquired to obtain multiple views of the subject 16 or to capture images corresponding to different relative positions of the subject 16 and the patterned illumination. An image of the reflected patterned illumination may be used to determine the size and shape of the target. Further, the topology of the subject 16, the patterned illumination, and the fluorescence emission may be used as inputs to a reconstruction algorithm to determine the location of and concentration of the target. In one example, the detector 34 may include one or more of a charged coupled device, an intensified charged coupled device, a time-gated charged coupled device, a gain-modulated charged coupled device, a complementary metal oxide semiconductor device, an electron bombardment charge coupled device, and an image intensifier tube. Further, intensified, gated, and modulated image intensifiers offer a convenient means for sampling large areas with appropriate temporal measurements.

Such a detector 34 may provide spatial resolution enabling simultaneous detection of optical signals emanating from different locations on the surface of the subject 16. Further, while using a source with multiple wavelengths, the CCD camera may facilitate dividing the light into constituent wavelengths at each given point on the surface of the subject 16. Further, the intensity of the light from the source 14 may be varied depending upon the sensitivity of the detector while remaining below levels that may cause damage to the tissue in the subject 16.

Figure 2:
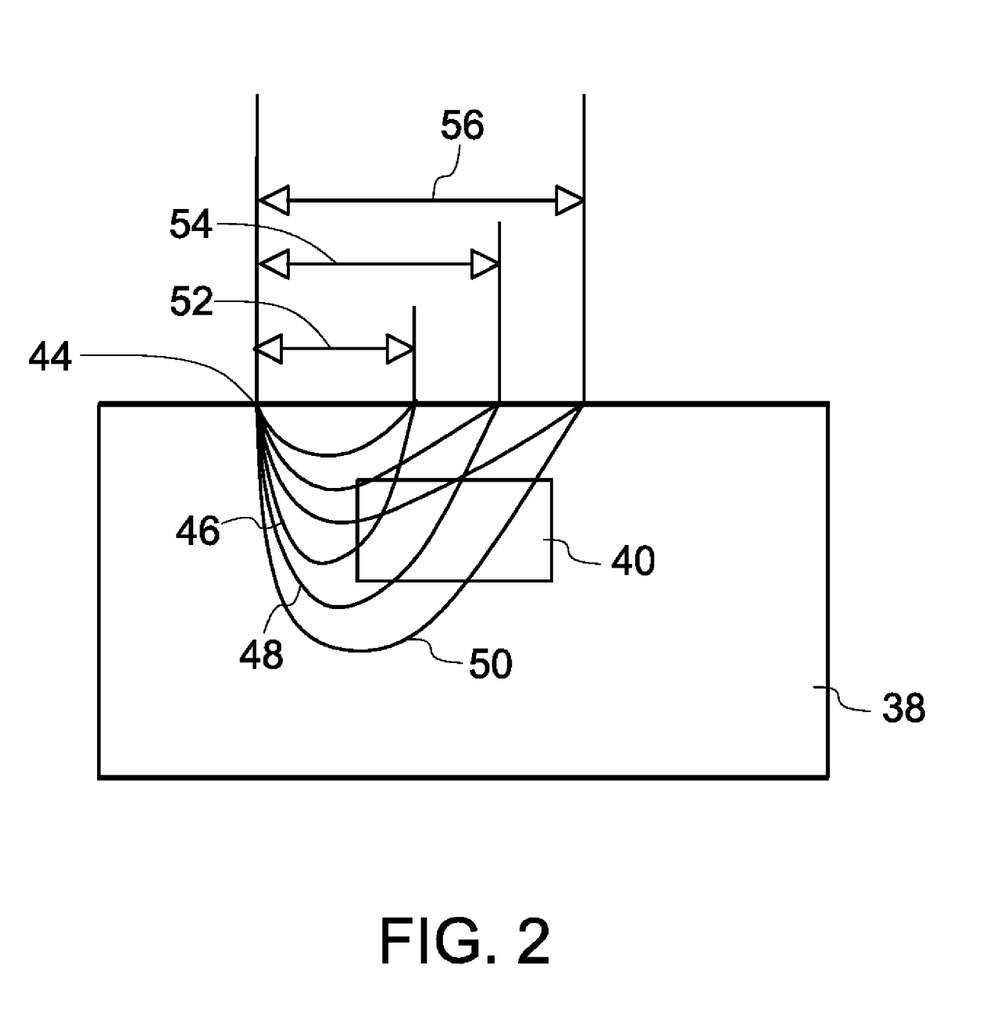
FIG. 2 is a two-dimensional view of a subject being exposed to excitation light from a point source, in accordance with embodiments of the present technique.

Turning now to FIG. 2, a two-dimensional (2D) view of a subject 38 is illustrated as a vertical, or a sagittal, cross-section through the subject and the target. The subject 38 includes a target 40 to be detected. The target 40 is disposed at a certain depth within the subject 38. The excitation light is emitted from a point source 44 for a 2D representation. For a three-dimensional (3D) representation of the subject 38, the point source 44 can be visualized as a line of illumination across the surface of the subject, going into the plane of the paper at the point 44. The excitation light penetrates at varying depths as illustrated by the light paths 46, 48 and 50. Depending on the depth of penetration of the corresponding excitation light, the emitted light emerges, on average, from the subject 38 at different distances from the point source 44 as represented by the reference numerals 52, 54 and 56. Therefore, area detection of the emitted light provides information about the depth of the target by enabling detection of emitted light from areas away from the illumination region, such as point 44, of the illustrated embodiment with the detection of emission from many different source to detector separations. Each pixel at a different distance from the source interrogates a different depth in the subject.

Figure 3:
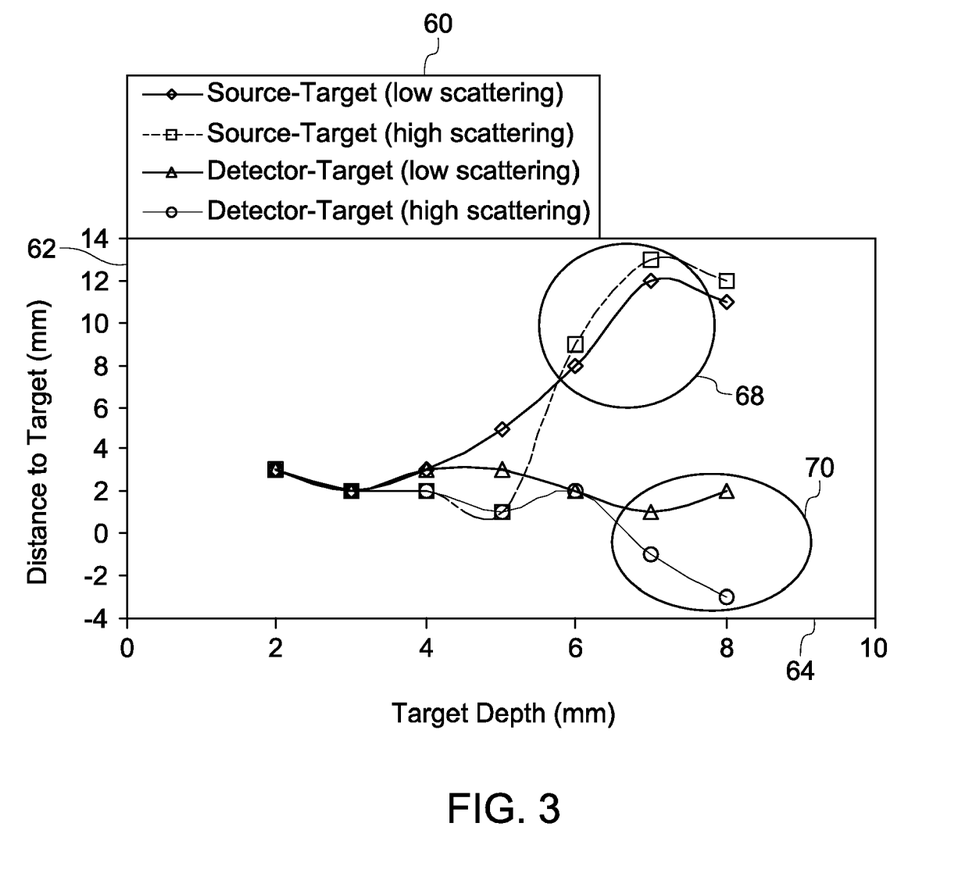
FIG. 3 is a graphical representation indicating a location of maximum sensitivity in terms of distance between the source and the target, and detector and the target with respect to the target depth, in accordance with embodiments of the present technique.

In a two-dimensional (2D) model of a scattering and absorbing tissue phantom with the two dimensions representing a line on the imaging surface and depth, the excitation source is defined as a single point. The model then predicts the emission at a line along the surface of the phantom model, each point representing a different source to detector separation. FIG. 3 shows the location of maximum sensitivity in terms of distance between the source and the target, and detector and the target with respect to the target depth represented by reference numeral 64. The illustrated embodiment demonstrates the usefulness of a patterned illumination and an area detection system to collect image frames pertinent to target depth reconstruction. The axis 62 represents the illumination source to target and detector to target distances using different legends 60. In the illustrated embodiment, the source and the target placed at a distance of approximately 3 mm provide maximum discrimination for a shallow point target. However, as targets get to a depth of 4 mm and deeper, sources at greater distances from the target provide more sensitive information about the target as illustrated by the points lying within the circle 68. In contrast, the maximum sensitivity of detection occurs as the distance between the target and the detector decreases as indicated by the points lying within the encircled region 70. In either case, the emitted light is collected away from the illumination region and the distance between the illumination region and a point on the surface of the subject from where the emitted light comes out of the subject increases with increase in target depth. The graphical representation of the illustrated embodiment is based on two-dimensional diffusion simulations for reduced scattering of 0.866/mm and 1.732/mm and absorption coefficient of 0.045/mm, 1 mM fluorescent dye in the target and a target to background ration of 50:1. The location of the minimum spatial derivative of the difference of log of emission fluence with and without the target is taken to represent the location of maximum sensitivity.

Figure 4:
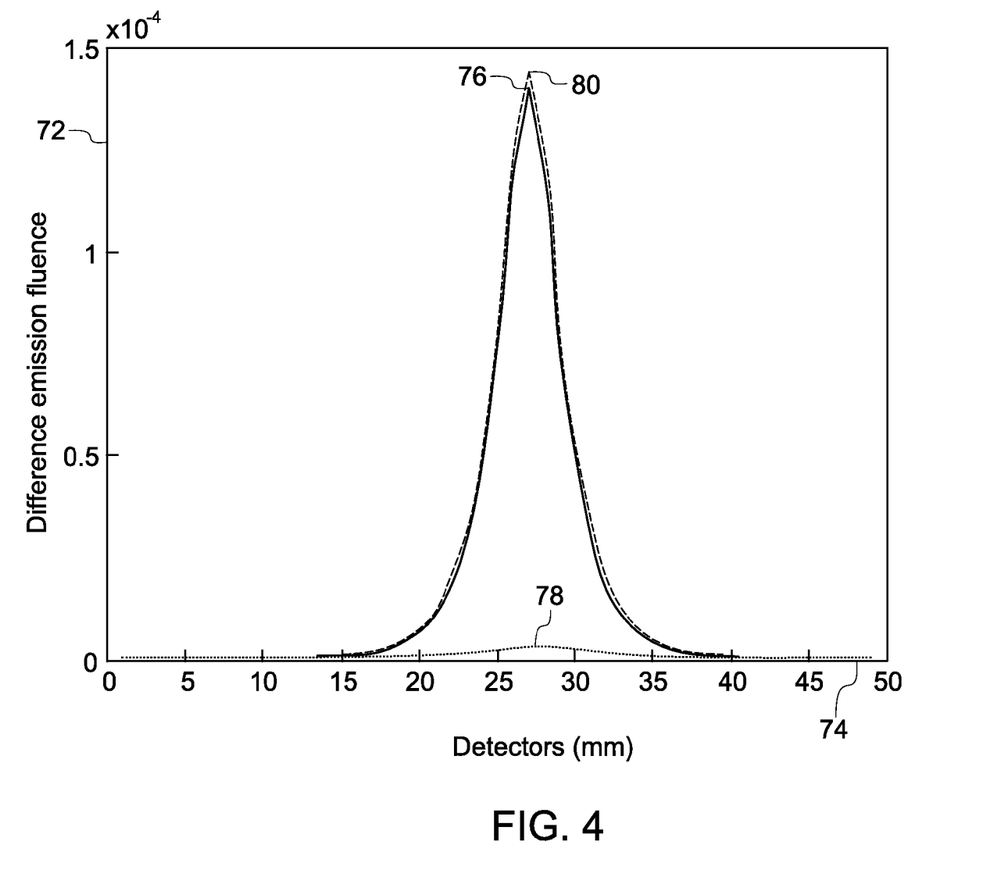
FIG. 4 is a graphical representation of emitted light for stacked targets; in accordance with embodiments of the present technique.

Referring now to FIG. 4, a graphical representation of difference of log of emission fluence with and without the target for stacked targets is illustrated. The graphs represent the detected difference in emission fluence on the y-axis represented by the reference numeral 72. The graph 76 represents the difference emission fluence for a 2 mm deep target, graph 78 represents the emission fluence for a 7 mm deep target, and graph 80 represents the collective difference emission fluence for stacked 2 mm deep and 7 mm deep targets. All the targets are located at 27 mm on the x-axis 74. Further, the source and target distance in the illustrated embodiment is about 3 mm. It should be noted that the graphs are based on two-dimensional diffusion simulations for reduced scattering of 0.866/mm and absorption coefficient of 0.045/mm, 1 mM fluorescent dye in the target and a target to background ration of 50:1. In the illustrated embodiment, an illumination source is located 3 mm from the target location. As evident from the nearly overlapping graphs 76 and 80, the detected emission is similar for the 2 mm deep target and for the 2 mm and 7 mm stacked targets.

Figure 5:
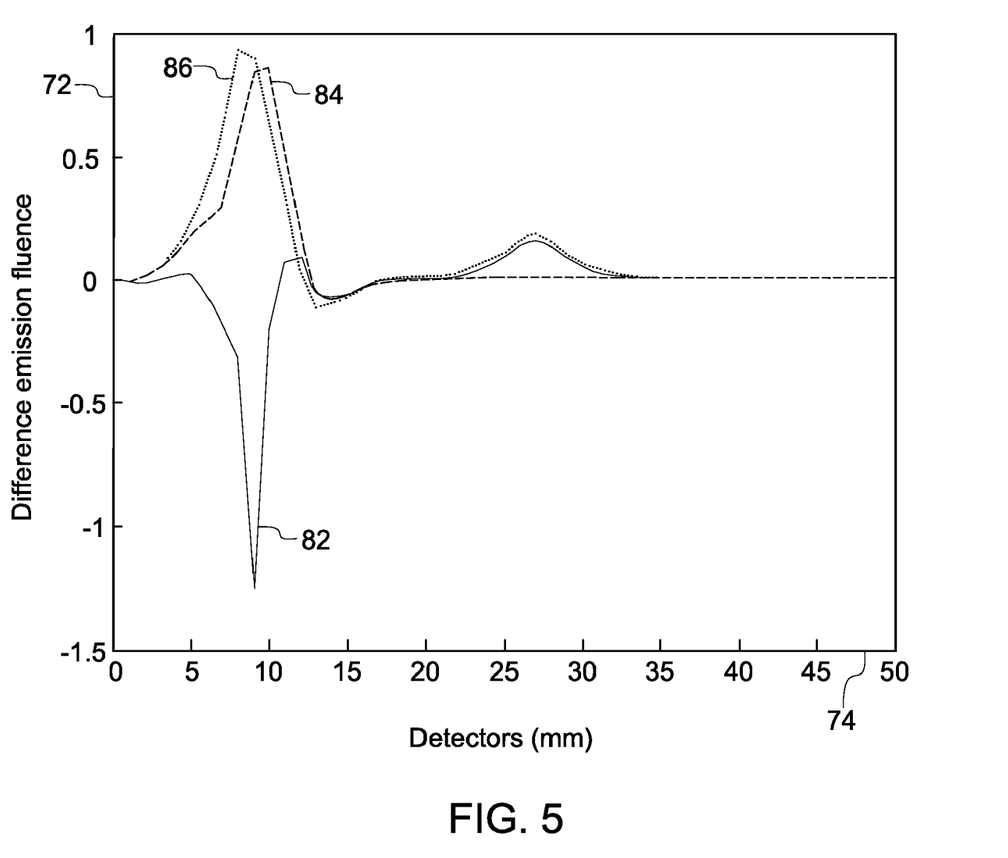
FIG. 5 is a graphical representation of detected emission fluence for the targets of FIG. 4 with an increased distance between the source and the target locations, in accordance with embodiments of the present technique.

FIG. 5 shows the detected difference of log of emission fluence with and without the target for the same targets as those of FIG. 4, however, in the illustrated embodiment, the distance between the source and the target location is increased to 18 mm. The graph 82 represents the difference emission fluence of the 2 mm deep target. The visibility of the 2 mm target decreases with the increase in source to target distance, as would be expected by referring to the illustration of FIG. 3. Further, the graph 84 represents the difference emission fluence of the 7 mm deep target, and the graph 86 represents the difference emission fluence of the stacked target. The location of peak emission fluence is different for the 7 mm target and the stacked 2 mm and 7 mm target. Thus different image frames in the region around the illumination source make optimum detection of the 7 mm and the stacked 2 mm and 7 mm targets. The positive peaks of the graphs 86 and 84 indicate association with the 7 mm deep target either in isolation or in the stacked case. Careful analysis of successive frames can help identify stacked targets using patterned illumination with the detected fluence from multiple illumination locations. Background signals that limit the sensitivity of imaging systems to clearly visualize embedded sources can come from non-specific distribution of dye proximal to the inclusion, or contributions from endogenous fluorescence. This method provides a means to account for and minimize the contribution from these sources, as well as to quickly sample a large number of photon paths through the tissue. The result is higher sensitivity, and greater information content than other continuous wave systems. This technique is also applicable to time and frequency domain methods for extracting more information such as fluorescence lifetime, quantum yield, concentration, photon path length, etc. Intensified, gated, and modulated image intensifiers offer a convenient means for sampling large areas with appropriate temporal measurements.

Image frames are recorded for each location of the patterned illumination on the subject. A similar problem can be posed with a computer simulation that predicts the resulting image from a target at some depth. A simulated image can be generated using a forward model for each combination of target depth and illumination region position. The correlation value of the detected image to the various simulated images would result in some peak correlation where the depth of the simulated target would represent the best estimate of the depth of the actual target. Some optimal source to detector separations may produce higher correlation values due to the detectability and depth of the actual target.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A method for fluorescence imaging of a target in a subject having a scattering medium, comprising:
   illuminating one or more points on a surface of the scattering medium using an illumination source, wherein the one or more illuminating points define an illumination region;
   collecting emitted light from the illumination region and an area away from the illumination region; and
   generating an image of the scattering medium using the emitted light.

2. The method of claim 1, wherein the illumination region is illuminated by a patterned illumination, wherein the patterned illumination comprises a point, an array of points, a line, an array of lines, a grid, a non-solid pattern extending along the surface, or combinations thereof.

3. The method of claim 1, further comprising filtering at least a portion of excitation light from the illumination region.

4. The method of claim 1, wherein the illumination source comprises a continuous light source, a pulsed light source, a light source with a time varying intensity, a light source with a time varying frequency, or a light source with a time varying phase.

5. The method of claim 1, further comprising administering a contrast agent into the scattering medium.

6. The method of claim 1, wherein collecting the emitted light comprises collecting the emitted light in a plurality of image frames while varying a location of the illumination region with respect to the subject, wherein each of the plurality of image frames corresponds to a particular position of the illumination region.

7. The method of claim 6, wherein varying the location of the illumination region comprises moving the illumination source relative to the subject.

8. The method of claim 6, wherein varying the location of the illumination region comprises moving the subject relative to the illumination source.

9. The method of claim 6, comprising identifying stacked targets by acquiring images from one or more illumination regions.

10. The method of claim 1, further comprising:
    detecting the emitted light while varying the position of the illumination region;
    generating a plurality of images corresponding to the different positions of the illumination region with respect to the subject;
    processing the plurality of images to generate an image of the scattering medium.

11. The method of claim 10, wherein processing the plurality of images comprises applying a reconstruction algorithm to image data.

12. The method of claim 1, comprising collecting the emitted light from more than one location on the surface of the subject.

13. A system for imaging a target in a subject, comprising:
    a source configured to illuminate at least a portion of a surface of the subject by a patterned illumination;

a full-field imaging detector configured to acquire emitted light from the illuminated portion of the subject and a region of the subject that is not directly illuminated; and a processor to transform the acquired emitted light into a display image.

14. The system of claim 13, wherein the full-field imaging detector is selected from a group consisting of a charged coupled device, an intensified charged coupled device, a time-gated charged coupled device, a gain-modulated charged coupled device, a complementary metal oxide semiconductor device, an electron bombardment charge coupled device, and an image intensifier tube.

15. The system of claim 13, wherein the source comprises a substantially monochromatic light source.

16. The system of claim 13, wherein the source comprises a continuous wave light source, a pulsed laser, a frequency modulated light source, an intensity modulated light source, or a phase varying light source, or combinations thereof.

17. The system of claim 13, further comprising illumination optics for directing the patterned illumination onto the surface of the subject.

18. The system of claim 13, further comprising collection optics for directing the emitted light to the detector.

19. A method for imaging targets in a subject, comprising:
illuminating a plurality of locations on a surface of the subject with a patterned illumination;
collecting corresponding emitted light in a plurality of image frames from areas within and away from illumination regions; and
generating an image of the scattering medium using the emitted light.

20. The method of claim 19, wherein collecting corresponding emitted light comprises varying a distance between the target and a detector.

21. The method of claim 19, further comprising employing a reconstruction algorithm to generate an image of the target.

* * * * *